United States Patent
Mills

(10) Patent No.: US 8,610,531 B2
(45) Date of Patent: Dec. 17, 2013

(54) MICROCOIL CONSTRUCTION

(75) Inventor: Gerald W. Mills, Palm Bay, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/402,333

(22) Filed: Feb. 22, 2012

(65) Prior Publication Data

US 2012/0150020 A1    Jun. 14, 2012

Related U.S. Application Data

(60) Division of application No. 12/825,789, filed on Jun. 29, 2010, now Pat. No. 8,146,239, which is a division of application No. 11/735,287, filed on Apr. 13, 2007, now Pat. No. 7,774,043, which is a continuation of application No. 09/736,529, filed on Dec. 13, 2000, now Pat. No. 7,210,223.

(51) Int. Cl.
*H01F 27/30* (2006.01)
*H01F 5/00* (2006.01)
*A61B 5/05* (2006.01)

(52) U.S. Cl.
USPC ........... 336/205; 336/200; 336/199; 336/197; 600/423; 600/422; 600/424

(58) Field of Classification Search
USPC .......... 336/205, 200, 199, 197; 600/422, 423, 600/424
See application file for complete search history.

(56) References Cited

U.S. PATENT DOCUMENTS

| | | | | |
|---|---|---|---|---|
| 4,709,472 A | * | 12/1987 | Machida et al. | 29/623.1 |
| 5,241,293 A | * | 8/1993 | Okumura | 336/183 |
| 5,349,744 A | * | 9/1994 | Takahashi | 29/602.1 |
| 5,409,558 A | * | 4/1995 | Takahasi et al. | 156/172 |
| 5,642,049 A | * | 6/1997 | Harada et al. | 324/318 |
| 5,791,409 A | * | 8/1998 | Flanders | 166/55.8 |
| 5,964,705 A | * | 10/1999 | Truwit et al. | 600/423 |
| 6,194,248 B1 | * | 2/2001 | Amaya et al. | 438/110 |
| 6,311,389 B1 | * | 11/2001 | Uosaki et al. | 29/605 |

* cited by examiner

*Primary Examiner* — Elvin G Enad
*Assistant Examiner* — Kazi Hossain
(74) *Attorney, Agent, or Firm* — Harness, Dickey & Pierce, PLC

(57) ABSTRACT

A microcoil is manufactured by rolling a trace unit in such a way as to form at least one winding. The trace unit is comprised of a conductive trace attached to a flexible insulating film. A preferred embodiment of the microcoil contains both a first winding and a second winding electrically connected and spaced apart by ajoining portion. The microcoil may be used for internal magnetic resonance imaging of patient by attaching the microcoil to a catheter.

19 Claims, 8 Drawing Sheets

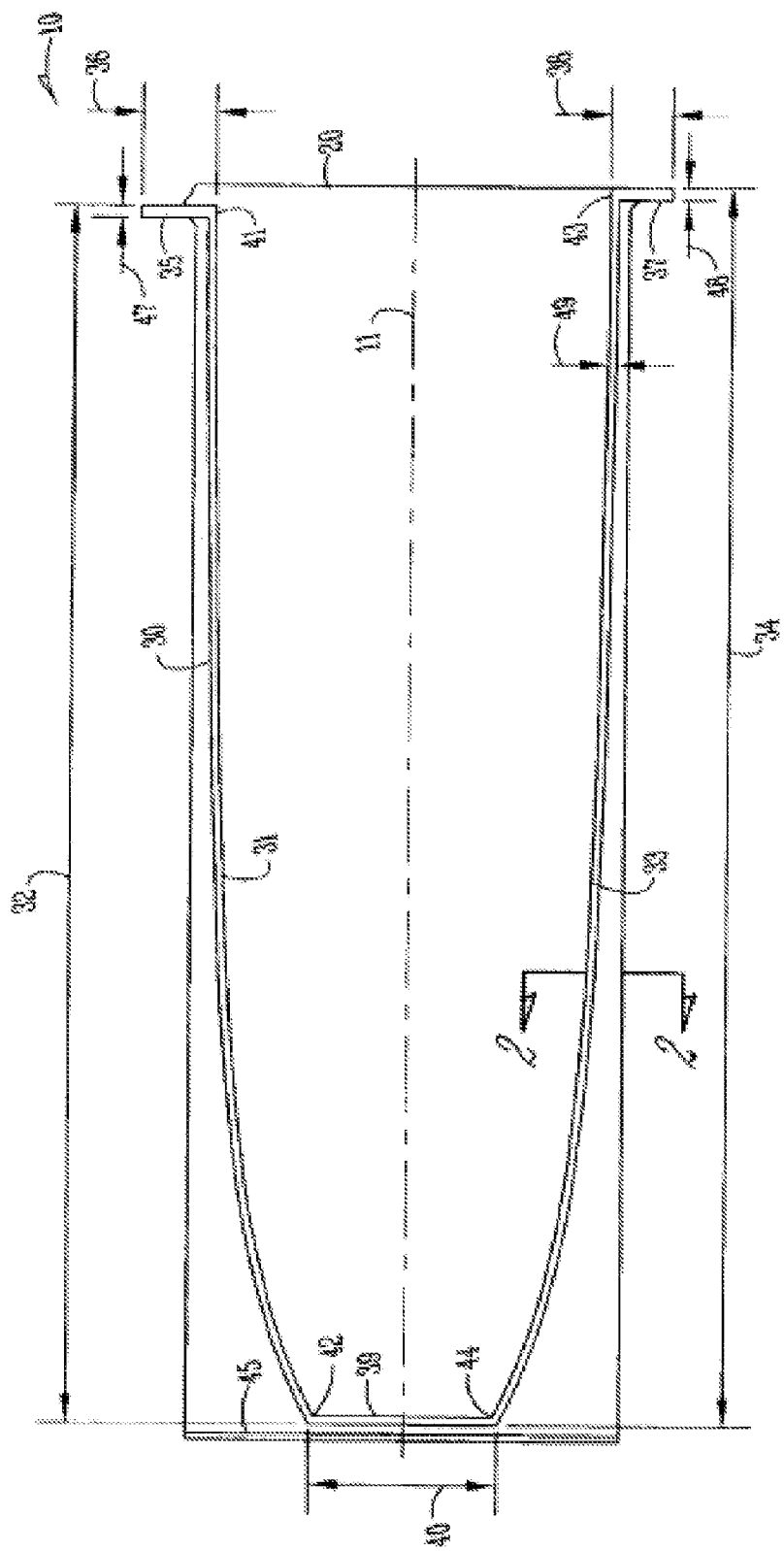

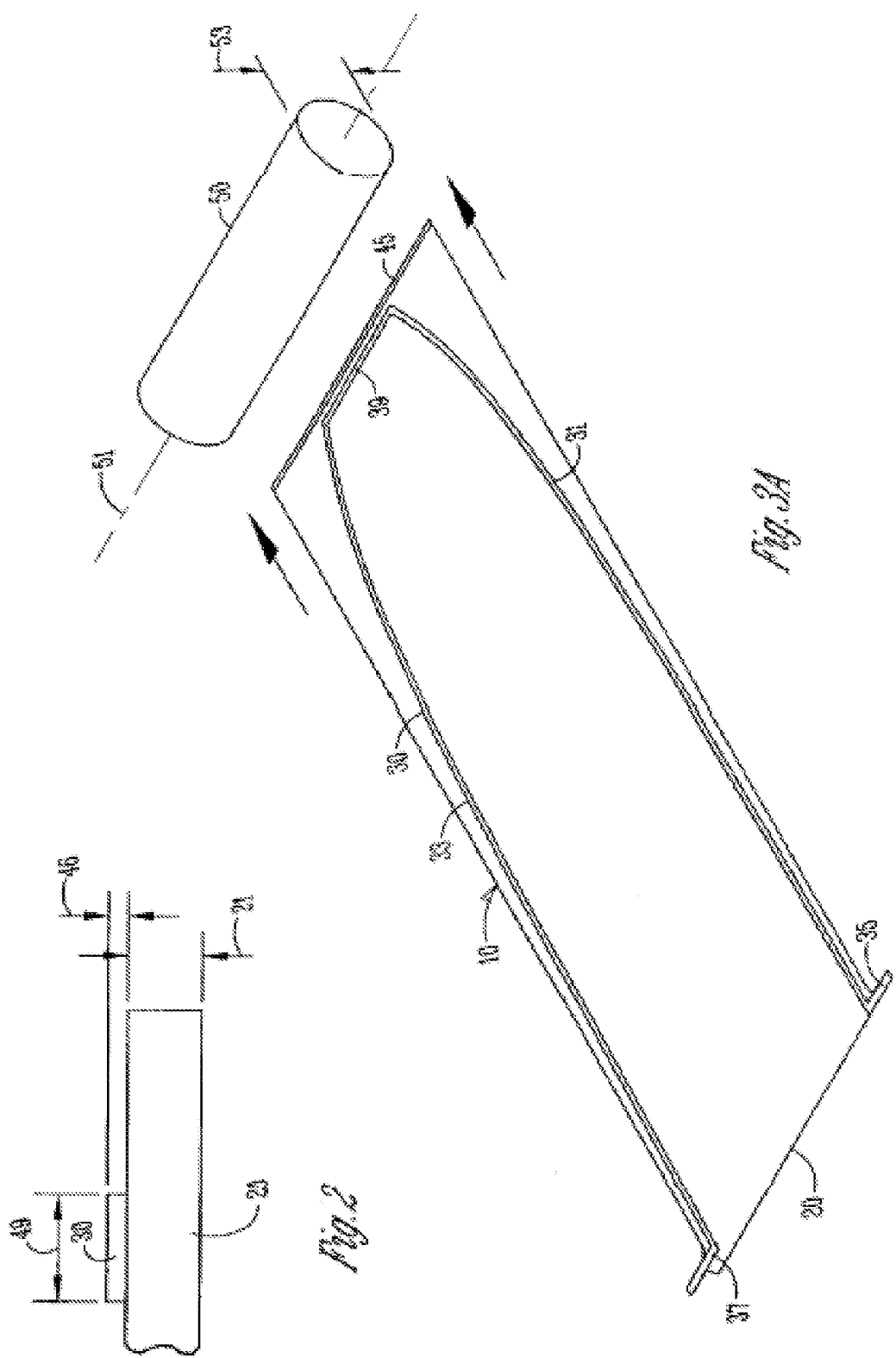

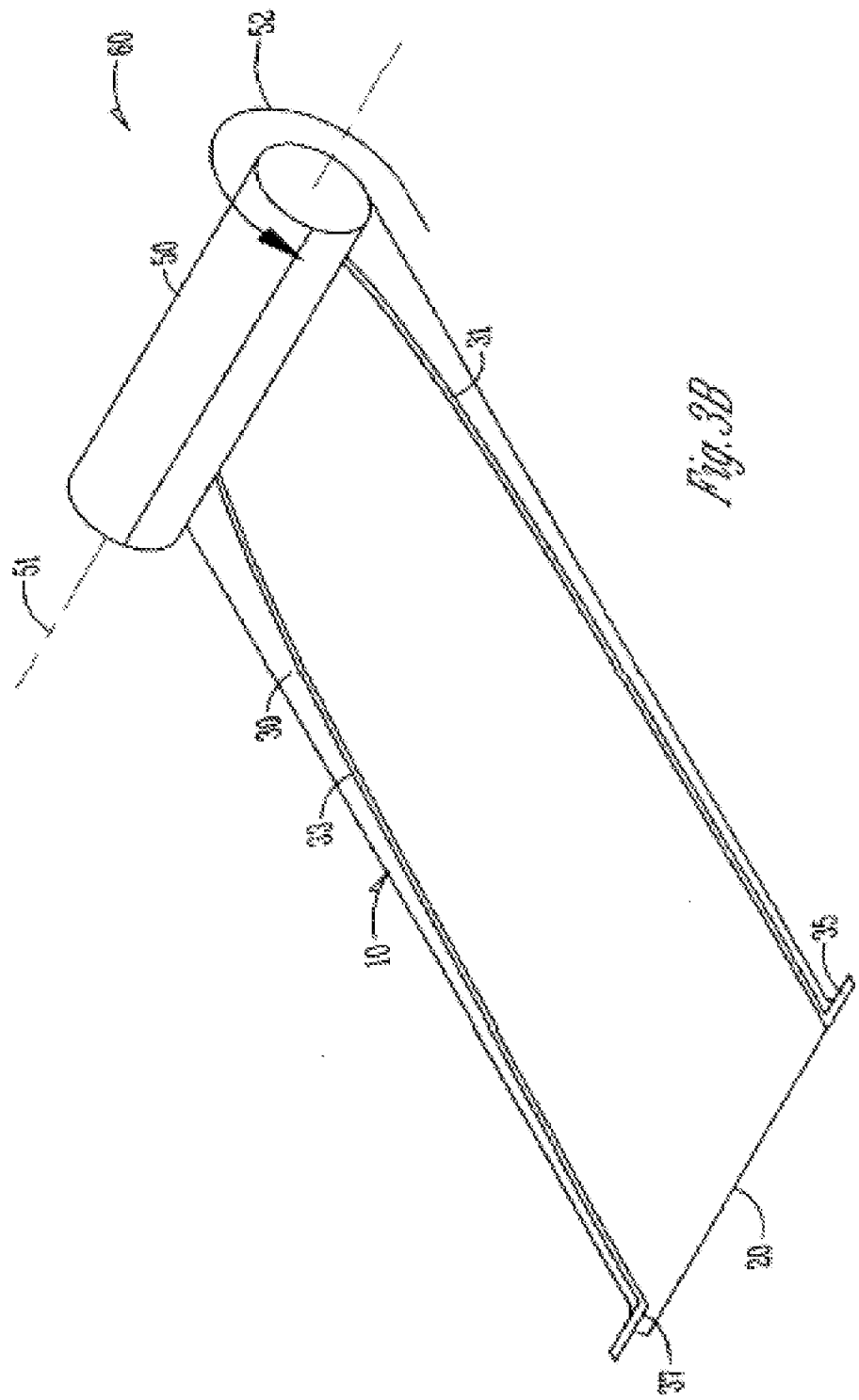

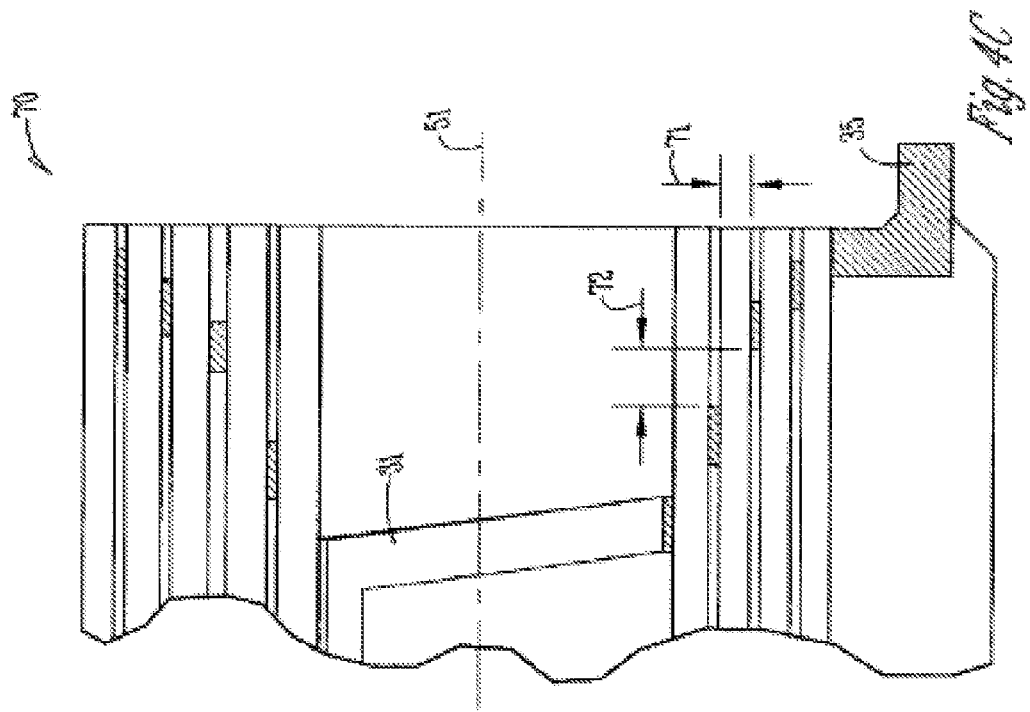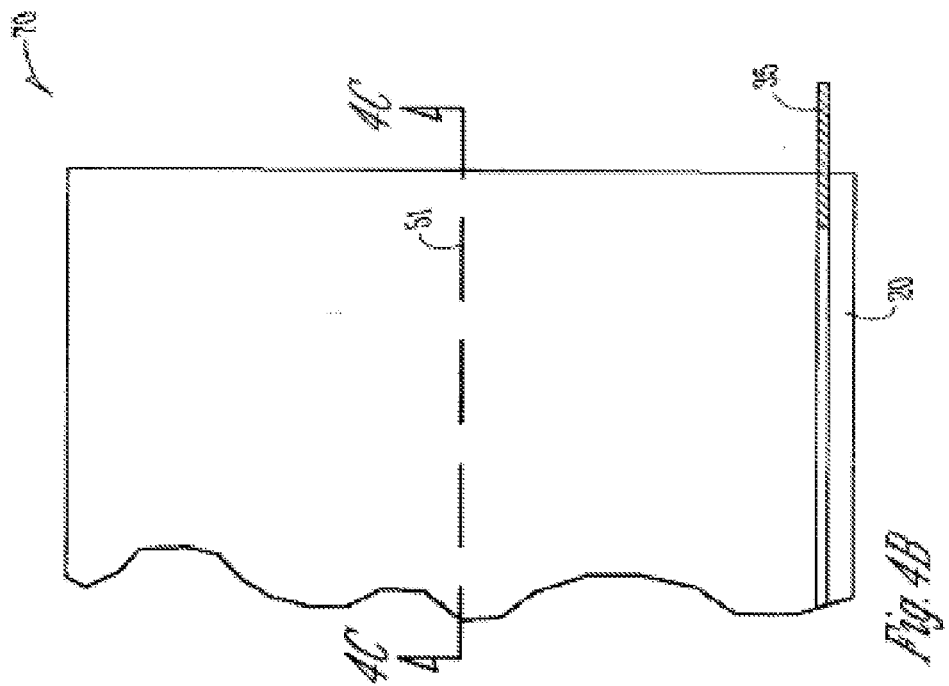

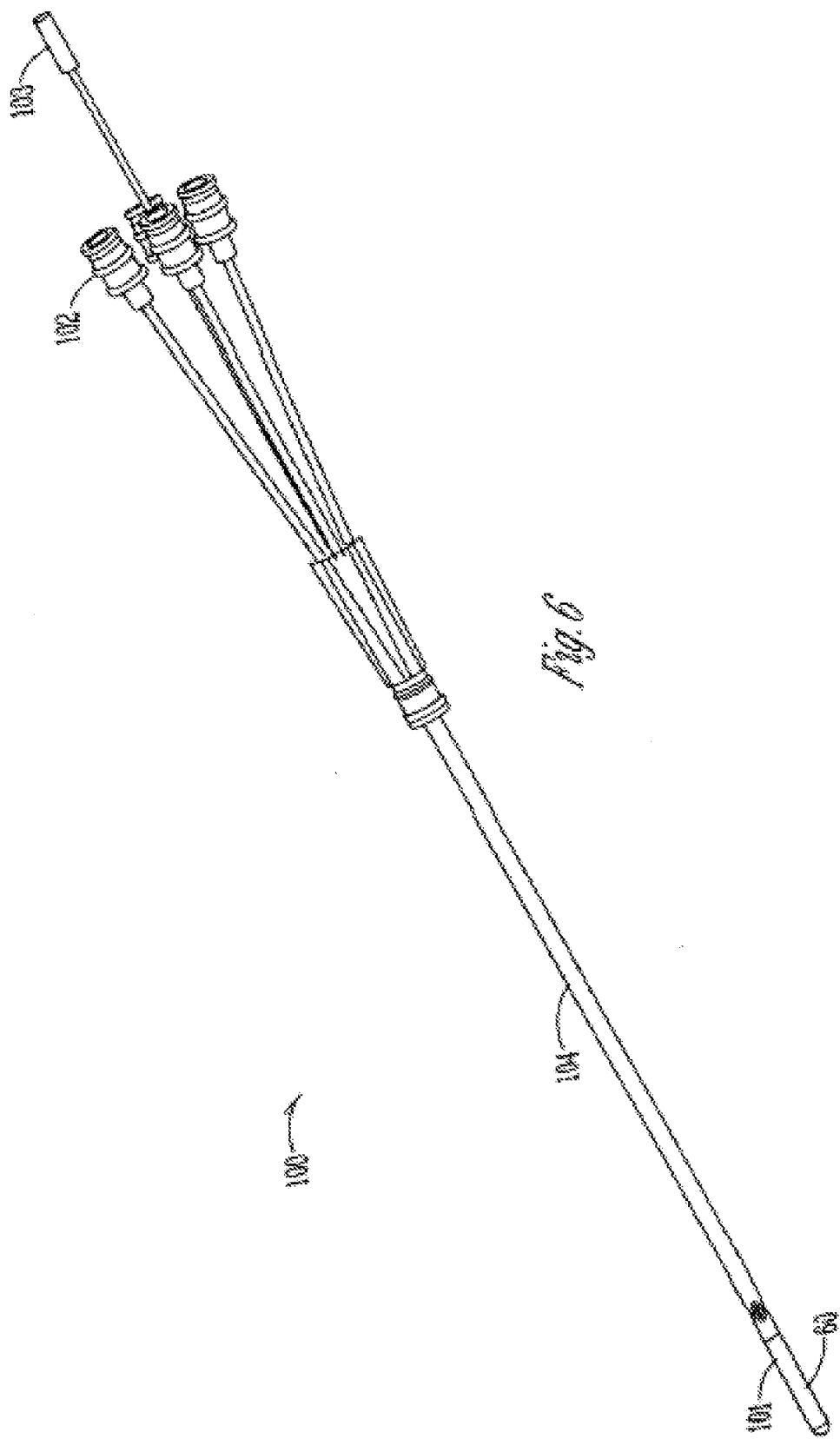

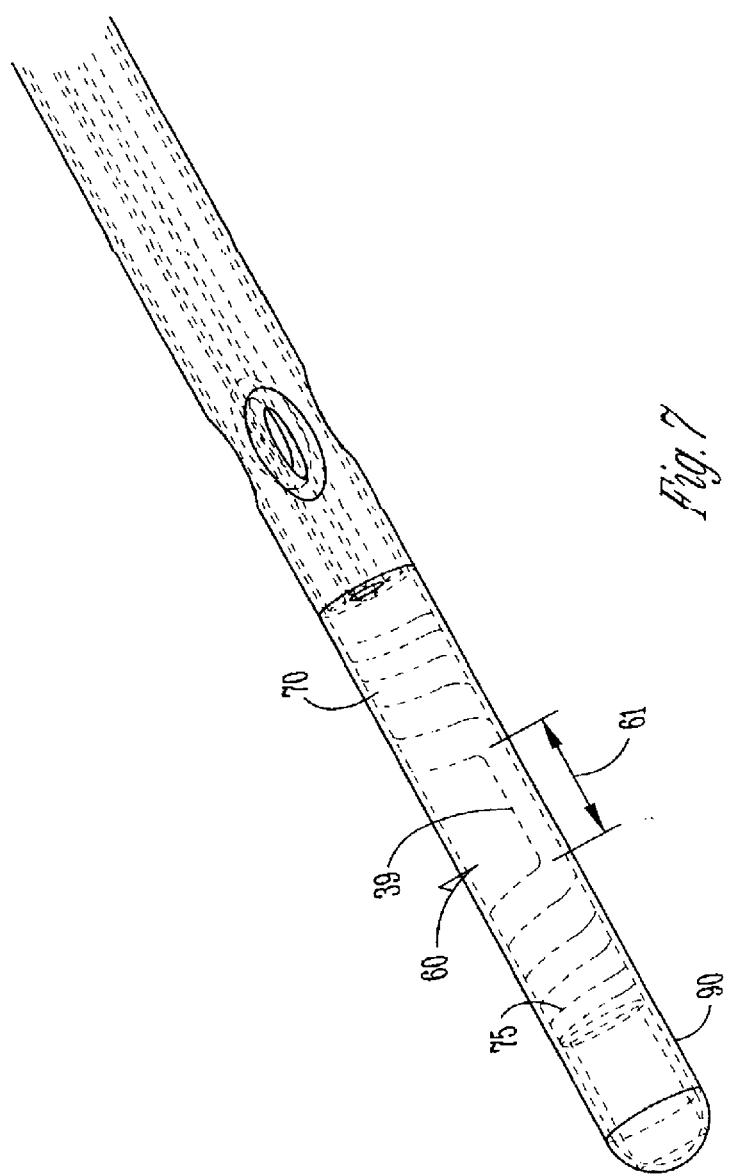

MICROCOIL CONSTRUCTION

CROSS-REFERENCE TO RELATED APPLICATIONS

This application is a divisional of U.S. patent application Ser. No. 12/825,789 filed Jun. 29, 2010, which is a divisional of U.S. patent application Ser. No. 11/735,287 filed Apr. 13, 2007, now U.S. Pat. No. 7,774,043 issued Aug. 10, 2010, which is a continuation of U.S. patent application Ser. No. 09/736,529 filed Dec. 13, 2000, now U.S. Pat. No. 7,210,223 issued May 1, 2007. The entire disclosures of the above applications are incorporated herein by reference.

FIELD OF APPLICATION

This invention relates to microcoils and their construction. Specifically, this invention relates to microcoils for use in medical devices used to obtain a magnetic resonance image of a region within a natural organism or patient (such as within a human) or elsewhere.

BACKGROUND

The use of magnetic resonance medical devices provides enhanced imaging within the region of interest and can be used for various internal procedures including targeted drug delivery. The term microcoil or MR microcoil is used to denote a magnetic resonance device used for imaging internally from a patient. This term is in contrast to MR coils that are conventionally used externally to the body for MR imaging purposes. A microcoil may contain one winding of electrical conductor, or multiple windings that are spaced a distance apart from each other. Typically multiple windings are joined together at a predetermined spacing with the planes of the windings parallel to each other.

The MR microcoil may be mounted at the tip of a catheter or other insertion device used to probe the interior of a body. The combination of the microcoil mounted on another device provides quick and direct access to the region where imaging is required. Medical procedures such as image-guided and minimal access surgery, performed within small regions of a patient's anatomy, demand the ability to visualize the internal terrain and/or the procedure being performed by the surgeon. While alternative methods, including x-ray imaging and fiber optic viewing offer possible alternative means of performing the visualization of terrain and the location of physical secondary devices, magnetic resonance imaging methods are a particularly convenient means of doing this, especially given the highly localized nature of the procedures being performed.

As with any manufactured device, new methods of manufacturing components are always being pursued to enhance performance and lower manufacturing costs. Conventionally, microcoils are manufactured by hand winding of an electrical conductor around a mandrel, or alternatively machine winding an electrical conductor around a mandrel. The resulting winding may have to be removed from the mandrel, and the leads for each end of the winding must be isolated. Additionally, where multiple windings are joined together in a device, the ends from multiple windings need to be connected. Handling windings in the manufacturing process can cause damage to the fragile windings resulting in manufacturing yield loss. The trend of smaller devices only increases this problem. With minimally invasive surgical procedures, the electrical conductor diameters used must be increasingly smaller to provide smaller coils. These coils are more easily damaged.

In manufacturing microcoils, there are also dimensional control variations within a single winding, and between windings. The diameter of the an electrical conductor used in a single winding may vary and affect the electrical characteristics of the resulting winding. Similarly, the insulating coating around the electrical conductor may vary in thickness and affect the electrical properties of the winding.

From one winding to another, variations in electrical conductor diameter and coating thickness are still a manufacturing variable. In addition, the number of turns from one winding to the next must be controlled by measuring the length of electrical conductor used in each winding. Also, the distance between windings in a microcoil containing multiple windings must be controlled by carefully joining the ends of a conventional winding at a measured distance.

While these conventional approaches to the manufacture of windings and microcoils result in functioning microcoils, the process is time consuming with several steps. Manufacturing yield is a problem due to the handling necessary in the conventional process, and consistent quality control is difficult.

SUMMARY

What is needed is a microcoil that can be manufactured more easily and which results in a more uniform microcoil with more consistent quality. What is also needed is a microcoil made by attaching a conductor onto an insulating film and configuring the film to form a winding or multiple windings. The manufacturing process of the microcoil requires minimal processing steps and minimal exposure to handling damage during processing. The process of manufacturing the microcoil is also conducive to tight quality control standards yet it is easily adapted to accommodate product design changes. The novel manufacturing process is capable of producing a novel microcoil that is extremely small and inexpensive, with a high manufacturing yield.

Microcoils produced by this process could be round or have other shapes depending on the mandrel or form that the film wraps around. A microcoil can be formed by soldering an end of the film to the mandrel and turning it to wrap the film into a winding. Multiple windings could also be included in one microcoil to make a series of connected windings.

In a further embodiment of the invention, the conductor is deposited as a trace onto the film using lithography and sputtering deposition techniques. The shape of the resulting microcoils is easily controlled by changing the mask pattern for the conducting trace deposited on the film. The electrical properties of the trace of conducting material are easily controlled by varying the trace material, and the width/thickness of the trace.

The microcoil might be applied with a medical device such as a catheter where the catheter is guided by magnetic resonance imaging using the microcoil. The microcoil might be further combined with other electrical devices nested at least partially inside the coil.

BRIEF DESCRIPTION OF THE FIGURES

FIG. 1 is a top view of a trace unit in a flat condition.

FIG. 2 is a sectional view along line 2-2 of the trace unit in a flat condition in FIG. 1.

FIG. 3a is a perspective view of a trace unit and a mandrel.

FIG. 3b is a perspective view of a trace unit being rolled onto a mandrel.

FIG. 4b is a front view of a single winding of a microcoil.

FIG. 4c is a sectional view along line 4c-4c of a single winding in FIG. 4b.

FIG. 6 is a perspective view of a catheter device.

FIG. 7 is a close up view of an end of a catheter device.

DESCRIPTION OF THE INVENTION

Figure 4A:
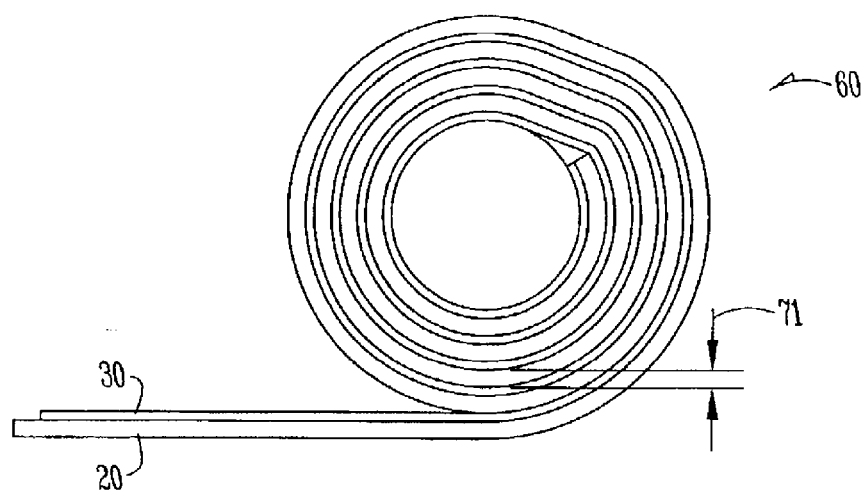
FIG. 4a is a side view of a microcoil.

A catheter 100 is shown in FIG. 6, is used to probe areas of interest inside a patient. The distal end 101 of the catheter 100 can be inserted by controls at its proximal end 102. In order to image the area of interest, and potentially steer the distal end 101 of the catheter to the desired location, it is helpful to include an MR microcoil 60 at the distal end 101 of the catheter 100. The microcoil 60 uses magnetic resonance imaging techniques to characterize the tissue in its immediate vicinity. Signals from the microcoil 60 are sent along a length 104 of the catheter 101 through an electrical channel 103 to the proximal end 102 of the catheter where they can be used by the surgeon to indicate where the distal end 101 of the catheter is, and what types of tissue are near the distal end 101.

Figure 5:
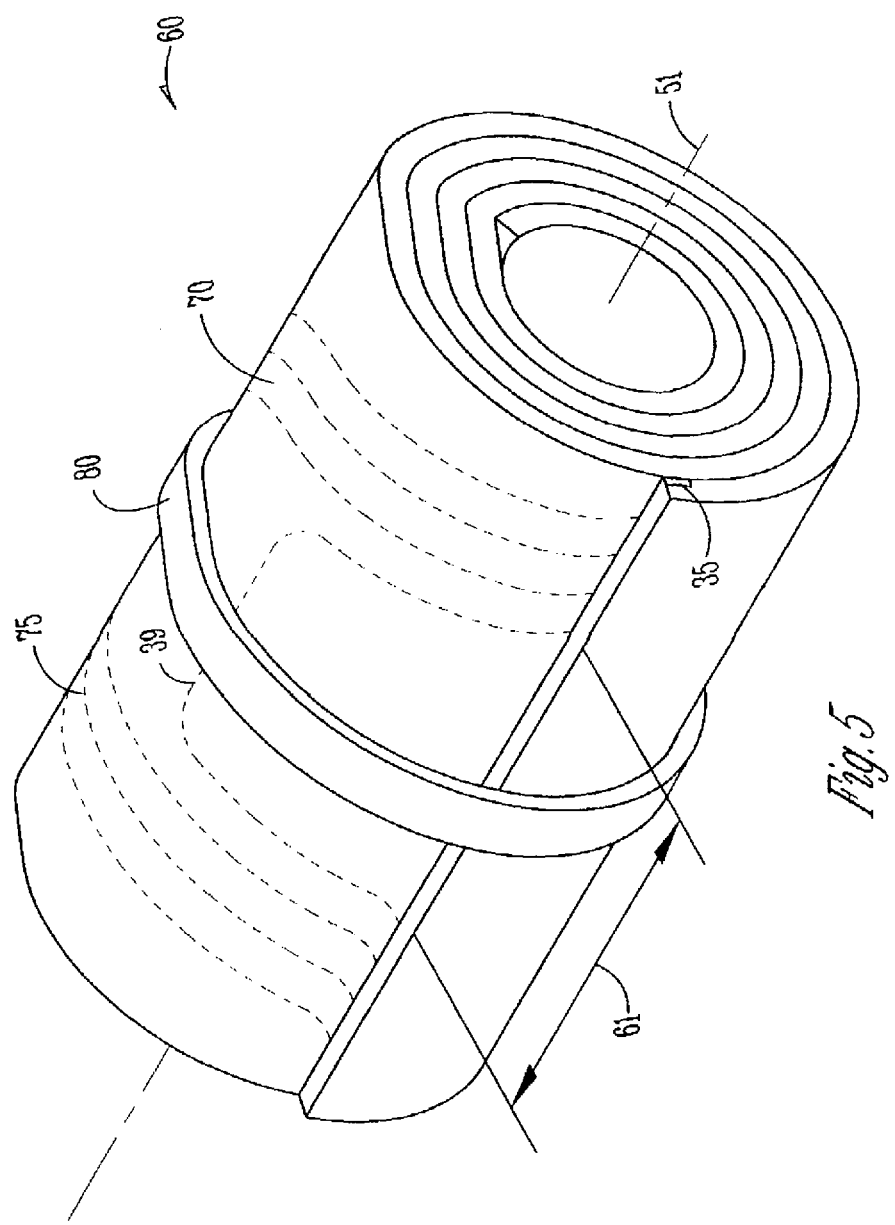
FIG. 5 is a perspective view of a microcoil.

A microcoil 60 as shown in FIG. 5 is manufactured by rolling a trace unit 10 as shown in FIG. 1 in such a way as to form at least one winding 70. A preferred embodiment of the microcoil 60 contains both a first winding 70, and a second winding 75 electrically connected and spaced apart by a joining portion 39. The microcoil 60 and method for forming the microcoil 60 are described in detail below.

FIG. 1 shows a trace unit 10 that is comprised of a flexible film 20, a conducting trace 30, and an attaching trace 45. As shown in FIG. 2, the flexible film 20 has a thickness 21 and the conducting trace 30 has a thickness 46. In a preferred embodiment, the thickness 21 and the thickness 46 are constant across the trace unit 10, however, the thickness 21 and the thickness 46 may vary in alternate embodiments. The flexible film 20 may have several shapes. It may be continuous, or it may contain openings in the film in areas other than where it supports the conducting trace 30.

Looking again at FIG. 1, the conducting trace 30 can be further broken down into a first leg 31 having a first leg length 32 and a second leg 33 having a second leg length 34. The first leg 31 has a lead end 41 and a joining end 42, and the second leg 32 also has a lead end 43 and a joining end 44. The first leg 31 and the second leg 33 have a trace width 49, which is uniform throughout the legs in a preferred embodiment.

The first leg 31 and the second leg 33 are substantially parallel to a trace unit axis 11 of the trace unit 10. However, as shown in FIG. 1, they are not exactly parallel to the trace unit axis 11. The legs 31 and 33 are shown in a preferred embodiment in FIG. 1 as having a slight curve, with the curve being more pronounced near a joining portion 39. The orientation of the legs 31 and 33 as shown in FIG. 1 is only one preferred embodiment. One skilled in the art would recognize that several configurations of legs would be possible to form other preferred embodiments without departing from the scope of the invention.

The conducting trace 30 also includes a first lead 35 and a second lead 37, having a first lead length 36 and a second lead length 38, and a first lead width 47, and a second lead width 48. The width of trace elements such as the legs and leads can be varied between elements, and within elements to alter the electrical characteristics of the trace. For example, a lead 35 could be wider than a leg 31, or a leg 31 could have a varying width along its length 32.

The first and second leads 35, 37 are attached to the first and second legs 31 and 33 at the first and second leg lead ends 41 and 43 respectively. The leads 35 and 37 may alternatively be attached elsewhere along the conducting trace 30 without departing from the scope of the invention. Supplemental leads (not shown) may also be electrically connected to the conducting trace to give device feedback or insert device instructions. The two legs 31 and 33 are joined at their respective joining ends 42 and 44 by a joining portion 39 of the conducting trace 30. The joining portion 39 has a length 40.

The trace unit 10 also includes an attaching trace 45 located adjacent to the joining portion 39. The attaching trace 45 is electrically isolated from the conducting trace 30. In a preferred embodiment, the attaching trace 45 is parallel with the joining portion 39 of the trace unit 10. In a preferred embodiment, the attaching portion is also substantially perpendicular to the legs 31 and 33.

The conducting trace 30 is comprised of copper because of its high conductivity and ductility. The ductility allows the copper to be rolled without cracking or breaking or otherwise causing an electrical failure. Any other conducting material that satisfies these conditions would be acceptable. The flexible film is comprised of polyimide because it exhibits good insulating properties and is readily available. It is also flexible, and withstands the deposition process used to attach the conducting trace. Any other flexible insulating material would be acceptable.

The conducting trace is attached to the flexible film by using a sheet of conductor, adhesive, and a basic lithography or photolithography technique commonly known in the industry. First a sheet of copper is adhered to the flexible film using a suitable adhesive. A mask layer is then deposited onto the sheet of copper with a positive image of the conducting trace 30 and the attaching trace 45. The flexible film 20 and the mask layer are then exposed to an etching chemical capable of removing copper, which removes the copper in the unmasked regions of the sheet. Once the excess copper is removed from the flexible film 20, the mask layer is removed to leave behind only the flexible film 20, the conducting trace 30, and the attaching trace 45. While this method of attaching the conducting trace 20 and the attaching trace 45 is preferred, it should be noted that any of several methods for attaching, including sputtering, physical vapor deposition, chemical vapor deposition, or mechanical attachment could be used to produce the invention.

In alternative embodiments, additional layers of flexible insulator and areas of conducting material may be attached and deposited onto the flexible film 20. Additional layers of flexible insulator may be used to protect the conducting trace 30, or they may be used to isolate additional areas of conducting material from the conducting trace 30. Additional areas of conducting material may be used to form electrical devices such as capacitors, integral with the trace unit 10.

The trace unit 10 is next prepared for rolling by attaching the trace unit 10 to a mandrel 50 as shown in FIG. 3a. The mandrel 50 may be round or square or any of several variations in cross section. The mandrel 50 may also be solid or hollow. The mandrel 50 may be made from any of a number of materials such as plastic or glass or non-magnetic metal. The mandrel 50 may not include magnetic materials due to interference with the magnetic resonance imaging that the coils are designed for in end use. The mandrel 50 may also be made up of more than one material. In this embodiment, the mandrel 50 is a semi-rigid coaxial line that is comprised of silver-plated copper on its outside diameter. The semi-rigid coaxial line is electrically conductive which allows information from the coil to be transmitted back to the user through the coaxial line.

A preferred manufacturing process of the microcoil 60 begins when the trace unit 10 is attached to the mandrel 50 by soldering the attaching trace 45 to the outside diameter of the mandrel 50. The attaching trace 45 is soldered such that it is parallel with a longitudinal axis 51 of the mandrel 50. More importantly, the attaching trace 45 and mandrel 50 are oriented such that when rolled, the legs 31 and 33 of the conducting trace 30 form windings 70 and 75 as shown in FIG. 5. Although a mandrel 50 is used to roll the trace unit 10 in a preferred embodiment, the trace unit 10 may be rolled without using a mandrel 50 without departing from the scope of the invention.

In a preferred manufacturing process, once the trace unit 10 is attached to the mandrel 50, the mandrel is rolled about the longitudinal axis 51 in direction 52 as shown in FIG. 3b. In a preferred embodiment, the rolling of the trace unit 10 about the mandrel 50 forms a microcoil 60 comprised of a first winding 70 and a second winding 75 as shown in FIG. 5, one winding formed from each leg 31 and 33. The joining portion 39 electrically connects the pair of windings 70 and 75. Alternative embodiments could form only one winding, which would not require a joining portion, or several windings could be formed, which would require multiple joining portions.

Design variations of the resulting microcoil 60 are easily accommodated with a preferred manufacturing process. The number of turns in the windings 70 and 75 may be controlled by varying the lengths 32 and 33 of the legs 31 and 33 respectively when forming the conducting trace 30 on the trace unit 10. Alternatively, the diameter 53 of the mandrel 50 that is chosen can be varied to change the resulting number of turns. Nine turns are used for a preferred embodiment.

As shown in FIG. 5, a longitudinal winding spacing 61 between windings 70 and 75 in the microcoil 60 is controlled by varying the length 40 of the joining portion or portions 39 when forming the conducting trace 30 on the trace unit 10.

FIG. 4a shows a side view of the microcoil 60. In this side view only the first winding 70 of the microcoil 60 is visible. The first winding 70 is further shown in FIG. 4b and sectional view 4c of FIG. 4b. As shown in FIG. 4c, within a given winding, a radial trace spacing 71 is controlled by selecting or varying the thickness 21 of the flexible insulating film 20. Also, a longitudinal axis trace spacing 72 is controlled by varying the shape and orientation of the legs 31 and 33 on the trace unit 10.

As shown in FIG. 3a, the legs 31 and 33 are substantially perpendicular to the longitudinal axis of rolling 51. However, the degree of perpendicularity varies along the legs 31 and 33. In a preferred embodiment, a given portion of a leg near the attaching trace 45 is less perpendicular to the longitudinal axis of rolling 51 than a portion of a leg proximal from the attaching trace 45. For example, the orientation of a generally linear leg could be varied such that the angle the generally linear leg makes with the longitudinal axis of rolling is more or less than 90 degrees. The shape of a leg could also be varied such that a leg is more linear or more arc shaped. These shape and orientation variations translate into variations of the longitudinal axis trace spacing 72.

Once the rolling of the trace unit 10 is complete, a microcoil 60 has been formed. A temporary retaining band 80 may then be placed around the microcoil 60 to hold its shape during the final placement of the microcoil 60 into its associated medical device. After the leads 35, 37 and possibly supplemental leads have been electrically connected to the medical device, the temporary band 80 may be removed. A more permanent protective oversleeve 90 as shown in FIG. 7 is then used to protect the microcoil and to hold its shape. If needed, other electrical component such as capacitors (not shown) may be embedded or partially embedded inside the structure of the microcoil 60.

As shown in FIGS. 6 and 7, a catheter device 100 is used in a preferred embodiment. The catheter device 100 has a distal end 101 and a proximal end 102. The microcoil 60 is located at the distal end 101 of the catheter. In operation, data from the microcoil travels along the length 104 of the catheter 100 through an electrical channel 103. A continuing electrical channel such as a coaxial line (not shown) transmits the data from the electrical channel 103 to another device such as a monitor device. This device receives information from the microcoil 60 concerning location of the distal end 101, or concerning the nature and condition of the tissue near the distal end 101.

Although specific embodiments have been illustrated and described herein, it will be appreciated by those skilled in the art that any arrangement which is calculated to achieve the same purpose may be substituted for the specific embodiment shown. This application is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A microcoil comprising:
 a coiled film of insulating material;
 a trace of conductive material attached to the film wherein the trace further comprises:
 a leg oriented on the film such that the leg circumferentially wraps around a longitudinal axis of the coiled film to form one or more windings, the leg progressively extends radially outward from the longitudinal axis;
 a first lead electrically coupled to the leg; and
 a second lead electrically coupled to the leg, whereby electricity may flow from the first lead, through the one or more windings of the leg and out to the second lead.

2. The microcoil of claim 1 wherein the trace of conductive material includes copper.

3. The microcoil of claim 1 wherein the film of insulating material includes polyimide.

4. The microcoil of claim 1 further comprising at least one supplemental lead electrically connected to the trace of conductive material.

5. The microcoil of claim 1, wherein the leg extends helically along the longitudinal axis.

6. The microcoil of claim 1, further comprising an attaching trace of conductive material that is electrically isolated from the trace of conductive material.

7. A microcoil comprising:
 a coiled film of insulating material;
 a trace of conductive material attached to the film wherein the trace comprises:

two or more windings electrically coupled together, each winding includes a leg oriented on the film such that each leg circumferentially wraps around a longitudinal axis of the coiled film, and progressively extends further from the longitudinal axis;

a first lead electrically coupled to the windings; and a second lead electrically coupled to the windings, whereby electricity may flow from the first lead, through at least a portion of the windings and out to the second lead.

8. The microcoil of claim 7 wherein the trace of conductive material includes copper.

9. The microcoil of claim 7 wherein the film of insulating material includes polyimide.

10. The microcoil of claim 7 further comprising at least one supplemental lead electrically connected to the trace of conductive material.

11. The microcoil of claim 7, wherein each leg progressively extends radially outward from the longitudinal axis.

12. The microcoil of claim 7, wherein each leg extends helically along the longitudinal axis.

13. The microcoil of claim 7, wherein the trace further comprises a joining portion that extends between and is electrically coupled to at least two of the legs.

14. The microcoil of claim 13, wherein the joining portion and the first lead are disposed on opposite terminal ends of the respective leg.

15. The microcoil of claim 13, wherein the joining portion extends substantially parallel to the longitudinal axis.

16. The microcoil of claim 7, wherein at least one of the first lead and the second lead extends substantially parallel to the longitudinal axis.

17. The microcoil of claim 7, further comprising an attaching trace of conductive material that is electrically isolated from the trace of conductive material.

18. The microcoil of claim 7, further comprising a retaining band that extends around the film and that retains the film in a coil.

19. A microcoil comprising:

a coiled film of insulating material that is coiled about a longitudinal axis;

an attaching trace of conductive material attached to the film, the attaching trace being substantially parallel to the longitudinal axis; and a conducting trace of conductive material attached to the film, the conducting trace being electrically isolated from the attaching trace, the conducting trace including:

a first leg oriented on the film such that the first leg circumferentially and helically wraps around the longitudinal axis and such that the first leg progressively extends radially outward from the longitudinal axis, the first leg including a first joining end and a first lead end;

a second leg oriented on the film such that the second leg circumferentially and helically wraps around the longitudinal axis and such that the second leg progressively extends radially outward from the longitudinal axis, the second leg including a second joining end and a second lead end;

a joining portion that extends between and is electrically coupled to the first joining end and the second joining end to electrically couple the first and second legs, the joining portion being substantially parallel to the longitudinal axis;

a first lead that is electrically coupled to the first lead end of the first leg, the first lead being substantially parallel to the longitudinal axis; and a second lead that is electrically coupled to the second lead end of the second leg, the second lead being substantially parallel to the longitudinal axis, whereby electricity may flow from the first lead, through the first leg, through the joining portion, through the second leg, and out to the second lead.

* * * * *